United States Patent [19]

Schwarz et al.

[11] Patent Number: 4,931,032
[45] Date of Patent: Jun. 5, 1990

[54] OCTADIENYL ACETATE SYNERGIST FOR THE GRAPE ROOT BORER PHEROMONE

[75] Inventors: Meyer Schwarz, Kensington; Jerome A. Klun, College Park, both of Md.; J.Wendell Snow, Warner Robins, Ga.

[73] Assignee: The United States of America as represented by the Secretary of Agriculture, Washington, D.C.

[21] Appl. No.: 247,547

[22] Filed: Sep. 22, 1988

[51] Int. Cl.$^5$ .................... A01N 37/02; A61K 31/22
[52] U.S. Cl. ........................................ 514/546; 424/84
[58] Field of Search .................. 514/529, 546; 424/84

[56] References Cited

PUBLICATIONS

Chem. Abstracts vol. 101, entry 6873n.
Meyer Schwarz et al., "(E,Z)-2,13-Octadecadien-1-ol Acetate. A New Pheromone Structure for Sesiid Moths," Tetrahedron Letters 24(10): 1007–1010 (1983).
J. Wendell Snow et al., "The Attraction of the Grape Root Borer, *Vitacea polistiformis* (Harris) (Lepidoptera: Sesiidae) to (E,Z)-2,13 Octadecadienyl Acetate and the Effects of Related Isomers on Attraction," J. Entomol. Sci. 22(4): 371–374 (1987).
J. H. Tumlinson et al., "Sex Pheromones and Reproductive Isolation of the Lesser Peachtree Borer and the Peachtree Borer," Science 185: 614 (1974).
M. W. Barry et al., "Attractivity of Pheromone Blends to Male Peachtree Borer, *Synanthedon exitiosa*," Environ. Entomol. 7(1): 1–3 (1978); Chem. Abstr. 88: 146 (1978).
Donn T. Johnson et al., "Status of Grape Root Borer (Lepidoptera: Sesiidae) Management and Feasibility of Control by Disruption of Mating Communication," MPEAAL 12(2): 1–7 (1981).

*Primary Examiner*—Joseph L. Schofer
*Assistant Examiner*—Peter F. Kulkosky
*Attorney, Agent, or Firm*—M. Howard Silverstein; John D. Fado; Curtis P. Ribando

[57] ABSTRACT

Addition of (Z,Z)-3,13 octadecadienyl acetate to the grape root borer, *Vitacea polistiformis* (Harris), pheromone (E,Z)-2,13 octadecadienyl acetate increases capture of males in sticky traps by three- to sevenfold. This new composition will provide and effective system for monitoring and controlling the grape root borer.

5 Claims, No Drawings

OCTADIENYL ACETATE SYNERGIST FOR THE GRAPE ROOT BORER PHEROMONE

BACKGROUND OF THE INVENTION

1. Field of the Invention

This invention relates to a compound which synergizes the behavioral responses of insects induced by their attractant pheromone. This compound may be used in combination with pheromones and insect control measures such as toxicants or traps. The compound may be used to decrease the amount of pheromone needed and improve efficiency of the traps.

2. Description of the Prior Art

Insect-produced volatiles, e.g., pheromones, may facilitate location of conspecifics for mating.

The first pheromones for clearwing moths were discovered by Tumlinson et al. [Science 185: 614–616 (1974)] when they found that (Z,Z)-3,13 octadecadienyl acetate [(Z,Z)-3,13 ODDA] and (E,Z)-3,13 octadecadienyl acetate [(E,Z)-3,13 ODDA] were the attractants for the peachtree borer, *Synanthedon exitiosa* (Say), and the lesser peachtree borer, *S. pictipes* (Grote & Robinson), respectively. Later, Barry et al. [Environ. Entomol. 7: 1–3 (1978)] found that the addition of small amounts of the (E,Z)-3,13 ODDA isomer greatly improved the attractiveness of (Z,Z)-3,13 ODDA to the peachtree borer. In 1983, Schwarz et al. [Tetrahedron Lett. 24: 1007–1010 (1983)] identified the sex attractant for the male grape root borer, *Vitacea polistiformis* (Harris) as (E,Z)-2,13 octadecadienyl acetate [(E,Z)-2,13 ODDA]. This report described for the first time an isomer other than the 3,13 acetates and alcohols that was attractive to clearwing moths.

SUMMARY OF THE INVENTION

We have now discovered that (Z,Z)-3,13 octadecadienyl acetate is an effective synergist for the insect pheromone (E,Z)-2,13 octadecadienyl acetate.

In accordance with this discovery, it is an object of the invention to provide new compositions for attracting insects as an aid to insect control measures.

A further object of the invention is to provide new means to synergize the effect of insect pheromones.

A further object of the invention is to provide a means for increasing the effectiveness of insect traps for monitoring or suppressing insect populations.

Other objects and advantages of this invention will become readily apparent from the ensuing description.

DETAILED DESCRIPTION OF THE INVENTION

The grape root borer is a major factor limiting commercial grape production in the eastern and southeastern United States. Effective means of control of this insect are required to extend grape cultivation in these areas.

The importance of olfaction in the behavior of insects is well known. Insect-produced volatiles, e.g., pheromones, facilitate location of conspecifics for mating. Pheromones, which may be attractive alone, may be enhanced or synergized.

With the identification of the grape borer pheromone in 1983, a tool was available to monitor insect populations for directing insecticide applications and evaluating control measures. The pheromone could also be potentially used in trap-out and mating disruption strategies. However, the pheromone is expensive, and no practical synergist is currently available for the pheromone.

A synergist is herein defined as a material that enhances the activity of other materials, so that the overall activity of the mixture is greater than the sum of the individual components.

An effective synergist for an attractant pheromone is useful in several ways:

1. A synergist improves population monitoring with the pheromone not only by increasing the attractiveness of the pheromone but also by modifying the sex ratio of the insects attracted.

2. A synergist improves attractiveness of the pheromone, thus facilitating trap-out and mating disruption strategies.

3. A synergist reduces the cost of insect control, since its addition to the pheromone in traps decreases the quantity of costly pheromone needed.

4. Insect populations may be controlled by combining an insecticide with the synergized pheromone composition.

It is well known in the art that small structural differences in pheromone and synergist molecules may have profound influence on the biological activity. For example, (Z,Z)-3,13 ODDA is not in itself an attractant for the grape root borer [D. T. Johnson et al., MPEAAL 12(2): 1 (1981)], but we unexpectedly found it to effectively synergize the attractive characteristics of the isomeric compound (E,Z)-2,13 ODDA.

Blends of pheromone and synergist were made from stock solutions of pure compounds in hexane. The total dosage of the various blends of attractants was held constant at 1 mg/trap. Traps containing the synergized pheromone were suspended from the top wire of the trellis about 1 m above ground level. All tests were conducted in commercial grape vineyards and were replicated several times.

As indicated in Table I below, the 99:1 ratio of (E,Z)-2,13 ODDA to (Z,Z)-3,13 ODDA was a very effective combination, as it increased capture over the pure (E,Z)-2,13 ODDA by ca seven times.

TABLE I

Capture of Grape Root Borer Males in Traps Baited with (E,Z)-2,13 Octadecadienyl Acetate and Small Quantities of (Z,Z)-3,13 octadecadienyl Acetate

| Treatment ratio[a] (mg of pheromone) | | Number captured |
|---|---|---|
| (E,Z)-2,13 ODDA: (%) | (Z,Z)-3,13 ODDA (%) | |
| 100.0 | 0 | 9 |
| 99.75 | 0.25 | 13 |
| 99.0 | 1.0 | 63 |
| 97.5 | 2.5 | 6 |
| 95.0 | 5.0 | 8 |
| 90.0 | 10.0 | 0 |

[a] All traps baited with 1 mg of total attractant.

Tests were conducted with 1 to 5% levels of (Z,Z)-3,13 ODDA with the (E,Z)-2,13 ODDA in a large vineyard near Moultrie, GA. The test was replicated four times and was conducted over 6 days. These data are shown in Table II as the mean numbers of males captured during the entire time period. Again, the 1% formulation was best, but it did not differ significantly from the 2% (Z,Z)-3,13 ODDA. However, it did capture three times more insects than the pure (E,Z)-2,13 ODDA.

TABLE II

Capture of Male Grape Root Borers with Various Formulations of (E,Z)-2,13 Octadecadienyl Acetate Mixed with Various Amounts of (Z,Z)-3,13 Octadecadienyl Acetate

| Formulation[a] | Mean capture[b] |
| --- | --- |
| 95:5 | 3.3a |
| 96:4 | 12.5b |
| 97:3 | 15.3b |
| 98:2 | 23.3bc |
| 99:1 | 37.0c |
| 100:0 | 12.0b |

[a]All traps baited with 1 mg of total attractant.
[b]Means in the same column followed by same letter are not significantly different (P = 0.05; Duncan's multiple range test).

The potency of these synergized pheromone compositions dictates that they be applied in conjunction with a suitable inert carrier or vehicle as known in the art. Of particular interest are those which are agronomically acceptable. Alcohols, glycols, ketones, esters, aqueous mixtures, and solid carriers such as clays or cellulose are illustrative of suitable carriers. The synergized pheromone compositions may be used in a number of ways, for example in combination with pesticides to kill the insects or in traps to monitor population changes. Other formulations and methods of use will be obvious to skilled artisans.

The synergized pheromone compositions encompassed herein are effective in attracting a variety of organisms. Without desiring to be limited thereto, pests of particular interest known to be susceptible to treatment are agronomically important insects, especially the male grape root borer, *Vitacea polistiformis* (Harris).

A typical synergized pheromone composition contemplated by this invention comprises (Z,Z)-3,13 octadecadienyl acetate, 0.25% to 4%, preferably 1%; (E,Z)-2,13 octadecadienyl acetate, 96% to 99.75%, preferably 99%, combined with a suitable amount of an inert carrier.

The following examples are intended only to further illustrate the invention and are not intended to limit the scope of the invention which is defined by the claims.

EXAMPLE 1

Materials (E,Z)-2,13 ODDA was purchased from Bedoukian Research Inc., Danbury, CT. (Z,Z)-3,13 was purchased from Chem Samples, Columbus, OH. Both compounds were analyzed on a glass capillary gas chromatography column coated with SP 2340 and found to be of greater than 99.5% purity. Rubber septa were obtained from Thomas Scientific, No. 1780J12, Philadelphia, PA, and "Pherocon 1C" sticky traps were purchased from Trece, Inc., Salinas, CA.

EXAMPLE 2

Test Procedure

Blends of pheromone (E,Z)-2,13 ODDA and synergist (Z,Z)-3,13 ODDA were prepared in hexane and pipetted onto rubber septa which were suspended from the tops of "Pherocon 1C" sticky traps. The traps were suspended about 1 m above ground level at the top of wire trellis in commercial vineyards in Moultrie, GA. Traps were separated by at least 50 m. After 6 days, the insects caught in the traps were counted. Data thus collected are shown in Table II.

It is understood that the foregoing detailed description is given merely by way of illustration and that modification and variations may be made therein without departing from the spirit and scope of the invention, which is defined by the claims.

We claim:

1. A composition for attracting the grape root borer, *Vitacea polistiformis* (Harris), comprising the insect pheromone (E,Z)-2,13 octadecadienyl acetate and a synergistically effective amount of (Z,Z)-3,13 octadecadienyl acetate, wherein the ratio of said acetates is in the range of about 99.75:0.25 to 99:1, respectively.

2. An insect trap comprising a trapping means and a composition as described in claim 1 in an amount effective to attract the grape root borer to said trapping means.

3. A method of disrupting communication in the grape root borer comprising applying to the habitat of said borer a synergized insect pheromone composition as described in claim 1.

4. An insecticidal composition for controlling the grape root borer comprising an insecticide and a composition as described in claim 1 in an amount effective to attract said borer to said insecticidal composition.

5. A method of increasing the effectiveness of the insect pheromone (E,Z)-2,13 octadecadienyl acetate by combining a synergistically effective amount of (Z,Z)-3,13 octadecadienyl acetate with said insect pheromone, wherein the ratio of said acetates is in the range of about 99.75:0.25 to 99:1, respectively.

* * * * *